United States Patent [19]

Lund

[11] Patent Number: 5,401,868

[45] Date of Patent: Mar. 28, 1995

[54] ARYLOXYMETHYLCARBONOCHLORIDATE ESTER INTERMEDIATES FOR USE IN SYNTHESIZING PRO DRUGS AND THEIR USE THEREFOR

[75] Inventor: Frantz J. Lund, Lyngby, Denmark

[73] Assignee: Leo Pharmaceutical Producgts, Ltd. A/S (Lovens Kemiske Fabrik Produktionsaktieselskab), Ballerup, Denmark

[21] Appl. No.: 835,444

[22] PCT Filed: Nov. 28, 1990

[86] PCT No.: PCT/DK90/00308

§ 371 Date: Feb. 26, 1992

§ 102(e) Date: Feb. 26, 1992

[87] PCT Pub. No.: WO92/07263

PCT Pub. Date: Apr. 30, 1992

[30] Foreign Application Priority Data

Jan. 22, 1990 [GB] United Kingdom ............... 9001405

[51] Int. Cl.$^6$ ............... C07C 69/63; C07C 69/62; C07C 69/96; A61K 31/60
[52] U.S. Cl. ............... 558/280; 544/335; 546/318; 546/326; 548/201; 548/236; 548/334.5; 548/531; 548/535; 549/71; 549/484; 549/486; 538/282; 538/248
[58] Field of Search ............... 558/280, 282; 549/484, 549/486, 71; 548/201, 236, 334.5, 531, 535; 546/318, 326; 544/335

[56] References Cited

U.S. PATENT DOCUMENTS

| | | | |
|---|---|---|---|
| 3,479,328 | 11/1969 | Nordstrom | 558/280 X |
| 3,769,271 | 10/1973 | Southard | 558/280 X |
| 4,199,526 | 4/1980 | Senet et al. | 558/280 X |
| 4,335,138 | 6/1982 | Wiersdorff et al. | 558/280 X |
| 4,497,809 | 2/1985 | Yoshinobu et al. | 558/280 |
| 4,568,391 | 2/1986 | Von Bonin et al. | 558/282 X |
| 5,221,754 | 6/1993 | Carpino et al. | 558/280 X |

FOREIGN PATENT DOCUMENTS

| | | |
|---|---|---|
| 112130 | 6/1983 | European Pat. Off. |
| 093548 | 11/1983 | European Pat. Off. |
| 0287922 | 12/1970 | U.S.S.R. ............... 558/280 |

OTHER PUBLICATIONS

Jose Alexander et al, "(Acyloxy) alkyl Carbamates as Novel Bioreversible Prodrugs for Amines; Increased Permeation through Biological Membranes", J. med Chem, vol. 31, 1988, pp. 318, 322 the whole article.

F. H. C. Stewart, "Formation of Depsipeptide Ester Bonds by Accelerated . . . ", Chemistry and Industry, 1967, pp. 1960–1961 the whole article.

*Primary Examiner*—Floyd D. Higel
*Attorney, Agent, or Firm*—Cushman Darby & Cushman

[57] ABSTRACT

The present invention relates to hitherto unknown intermediate of formula, in which $R_1$ stands for hydrogen or a straight or branched aliphatic $C_1$–$C_{20}$ carbon chain or an aryl or aralkyl group, aryl and "ar" meaning an aromatic or heterocyclic, 5- or 6-membered ring substituent containing 1 or 2 hetero atoms selected among O, S and N, $R^1$ optionally being further substituted, and its chain being interrupted by hetero atoms like oxygen, or by carbonyl group(s); and $R^3$ stands for hydrogen or $C_1$–$C_3$ alkyl. The present intermediates can be used in a one step method for producing prodrugs of formula, where D-H = drug itself.

7 Claims, No Drawings

ARYLOXYMETHYLCARBONOCHLORIDATE ESTER INTERMEDIATES FOR USE IN SYNTHESIZING PRO DRUGS AND THEIR USE THEREFOR

The present invention relates to hitherto unknown intermediates of the below formula I for use in the synthesis of prodrugs.

In recent years, chemical modification of drugs into labile derivatives (prodrugs) with improved physico-chemical properties that enable better transport through biological barriers has become a useful approach for improving-drug delivery. Such transformation is often practised on ionizable molecules containing e.g. a carboxylic acid, an amino, or a hydroxy group that can be utilized for derivatization, in order to modify their ionization at physiological pH and to render desirable partition and solubility properties.

A necessary requirement of this approach is that the said prodrug is non-toxic and, when administered to a warm-blooded animal including a human being, is enzymatically and/or chemically cleaved in such a manner as to release the drug at its target or site of activity, quantitatively and at a desirable rate, while the remaining cleaved moiety remains non-toxic and is metabolized in such a manner that non-toxic metabolic products are produced.

It is, of course, also desirable that the prodrug can be provided without excessive costs in connection with its production, in particular without an appreciable loss of drug itself during its production and recovery, since the drug is usually the more expensive part of the prodrug.

The intermediate used to react with the drug in providing the prodrug should advantageously be stable and still be reasonably reactive.

In recent years, acyloxyalkoxycarbonyl derivatives have become interesting bioreversible prodrug moieties of drugs and medicaments which are more readily bioavailable than the drug itself, and further are less irritating to topical and gastric mucosal membranes and are more permeable through such membranes. An example of such prodrug is shown in the formula II

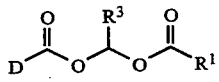
(II)

where D–H=the drug (D–H containing an OH, SH, NH$_2$ or a monosubstituted N function), and R$^1$COOH=non-toxic carboxylic acid, R$^1$ for instance meaning hydrogen or a straight or branched aliphatic C$_1$–C$_{20}$ carbon chain or an aryl or aralkyl group, aryl and 'ar' meaning an aromatic or heterocyclic, 5- or 6-membered ring substituent containing 1 or 2 hetero atoms selected among O, S and N. As examples of such aromatic or heterocyclic substituents, mention may be made of phenyl, furyl, thienyl, pyrrolyl, imidazolyl, thiazolyl, oxazolyl, pyridyl, and pyrimidinyl. R$^1$ may be further substituted, and its chain be interrupted by hetero atoms like oxygen, or by carbonyl group(s). R$^3$ means hydrogen or C$_1$–C$_3$ alkyl. Esters of this type have for instance been used as prodrugs of R$^1$COOH and have been shown to be enzymatically hydrolyzed in man. Obviously such esters will also liberate D–H.

Some esters of the formula II have been produced in a multi-step procedure, confer J. Med. Chem. 1988, 31, p. 318ff, where the drug (containing a primary or secondary amine group being the point of reaction) is reacted with a compound of formula III

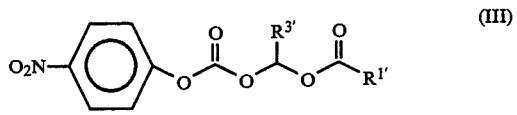
(III)

in which formula, R$^{1'}$ and R$^{3'}$ are hydrogen or lower alkyl.

The intermediates of formula III have the disadvantage of reacting rather slowly, if at all, when used in the production of prodrugs of formula II (Chemistry and Industry, 1967, p. 1960). Also, they seem to-be non crystalline and not very stable and are therefore difficult and costly to use technically (purification by chromatography).

It has now surprisingly turned out that intermediates of the formula I

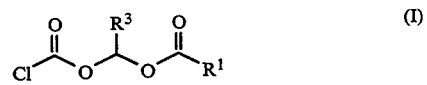
(I)

in which formula R$^1$ and R$^3$ have the above meanings can be provided which are both stable and of high purity following simple distillation or recrystallization, and which are still very reactive so that they can be used in a one step method for producing the desired prodrugs of the formula II in a high purity and without appreciable loss of the drug itself which is normally the most expensive part of the prodrug.

The intermediates of formula I, in which R$^3$ stands for hydrogen have been shown to be the more reactive and stable ones when used in the production of the desired prodrugs, and are thus the preferred ones according to the present invention.

It will be obvious to the man skilled in the art that, depending on the meaning of D or R$^1$ it may become necessary during the production of compounds of formula I or formula II to protect temporarily possible substituents reactive to acid chlorides and to remove the protective group(s) after reaction of I with D–H.

Also according to the invention, the intermediates of formula I (R$^3$=H) can be produced according to the following Scheme A (R$^1$ and R$^2$ having the above meanings)

Scheme A

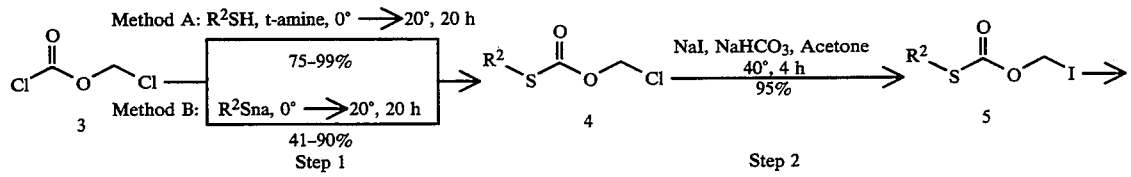

-continued
Scheme A

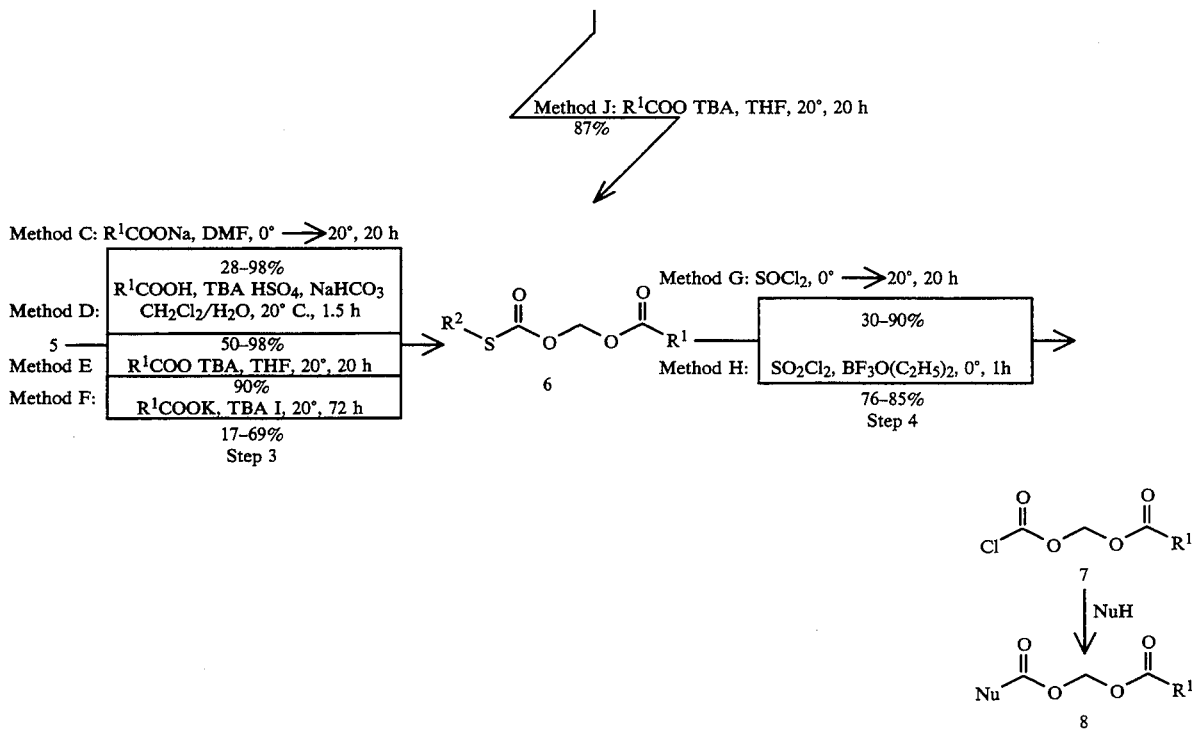

according to which the multifunctional chloromethyl carbonochloridate (3)—numbers in parentheses refer to numbers in the Scheme—is used as a starting material obtained by chlorination of methyl carbonochloridate or by treatment of formaldehyde with phosgene or with trichloromethyl carbonochloridate. The relationship between the reactivities of the two electrophilic centres in (3) is temporarily reversed by conversion of the acid chloride function to the less reactive carbonothioate group of (4). After utilization of the second chlorine atom for the formation of an ester (6), the acid chloride function of (7) (being the desired intermediate of formula I) is finally restored by chlorination.

It was known that the compound (3) could react with alcohols and phenols in the presence of pyridine to afford the derived alkyl or aryl chloromethyl carbonates, but this method did not work with alkylthiols. However, according to the present invention, when pyridine was replaced with a tertiary amine, such as triethylamine or diisopropylethylamine, and when an ethereal solution of a mercaptan $R^2SH$ and the tertiary amine was added to an ice-cold solution of (3) in ether, good to excellent yields (75–100%) of O-chloromethyl S-alkyl or S-aryl carbonothioates (4) could be obtained. Another possibility turned out to be the reaction of a suspension of $R^2SNa$ in ether with (3) affording varying yields (40–90%) of (4), the yields increasing with larger alkylthiols.

Before performing the reaction leading to an ester (6), the compound (4) was converted to its iodo analogue (5) by the Finkelstein reaction using sodium iodide at elevated temperature (40° C.), confer Scheme A, mostly in the presence of sodium hydrogen carbonate to neutralize traces of hydrogen iodide formed since addition of this base was found to preserve (5) from deterioration. Without this addition, (5b) became coloured in a few hours. Reaction in acetone at 40° C. for four hours with two equivalents of sodium iodide (and 0.1 equivalent of sodium hydrogen carbonate) was found to be optimal.

Due to their presumed instability, the crude liquid iodo compounds (5) obtained in almost quantitative yields were generally used immediately for the next step without any attempt at purification. However, the above mentioned addition of the preserving amount of the weak base showed to be sufficient to prevent deterioration of the iodo compounds, even when kept for years at −20° C.

The double esters (6) were mostly prepared by stirring a suspension of sodium carboxylate in dimethylformamide with the iodo compound (5) at room temperature for 20 hours. However, the use of liquid-liquid phase transfer conditions (method D in Scheme A) turned out to be the preferable method, the optimum being the addition for half an hour of the iodo ester (5) ($R^3=H$) at room temperature to a stirred mixture of tetrabutylammonium (TBA) hydrogen sulfate, sodium hydrogen carbonate, and carboxylic acid (1.3:2.6:1.3) in water and methylene chloride, 1,2-dichloroethane, or ethyl acetate followed by stirring for 1 hour. Simple carboxylic acids tend to give higher yields (80–100%) than carboxylic acids containing additional functional groups. Other methods are workable, confer e.g. Scheme A, methods E, F, and J (Examples 9, 10, and 14, respectively).

When purified by distillation, the double esters (6) were generally pure enough for subsequent conversion, in step 4 of Scheme A, to the desired intermediates (7) by restoring the acid chloride function through reaction with sulfuryl chloride, preferably in the presence of a catalytic amount of boron trifluoride etherate at −25°−−30° C. and subsequent stirring at 0° C. for one hour and half an hour at room temperature. The distillable compounds (7) were produced in high yields and could be kept without deterioration for years in a refrigerator.

The synthetic sequence is not restricted to acyloxymethyl carbonochloridates. By substituting 1-chloroalkyl carbonochloridates for (3) and treating the derived O-1-chloroalkyl S-alkyl carbonothioate with TBA butanoate in tetrahydrofuran for a suitable period of time, followed by sulfuryl chloride treatment provided a solution of 1-butanoyloxyalkyl carbonochloridate, but these intermediates seem to be less stable than (7).

The present intermediates of formula I can generally be prepared by reacting a 1-haloalkyl carbonochloridate of the formula IV $$\text{Cl}-\underset{\underset{R^3}{|}}{\text{CH}}-\text{OCOCl} \quad \text{(IV)}$$

where $R^3$ has the above meanings, is reacted with $R^2SR^4$, $R^2$ being $C_1$–$C_4$ alkyl, and $R^4$ being hydrogen or an alkali metal ion, to form a 1-haloalkyl carbonothioate of the formula V $$\text{Cl}-\underset{\underset{R^3}{|}}{\text{CH}}-\text{O}-\text{CO}-\text{SR}^2 \quad \text{(V)}$$

$R^2$ and $R^3$ having the above meanings, which is transformed into a 1-acyloxyalkyl carbonothioate of the formula VI $$R^1\text{COO}-\underset{\underset{R^3}{|}}{\text{CH}}-\text{OCO}-\text{SR}^2 \quad \text{(VI)}$$

$R^1$, $R^2$ and $R^3$ having the above meanings by reaction with a salt of a carboxylic acid $R^1$COOH, $R^1$ having the above meanings, and finally reacting the compound of formula VI with a chlorinating agent to yield the desired intermediate of formula I.

If, in formula I, $R^3$=H, the present intermediates are preferably being prepared by converting the compound of formula V to the corresponding iodide by reaction with sodium iodide, before transforming it via VI to I.

The preferred chlorinating agent used in the final step of the preparation of the present intermediates is sulfuryl chloride.

As mentioned above, it has surprisingly turned out that the present intermediates of the formula I can be provided in good yields and of reasonable costs, that they are stable, and even very reactive, in their intended use in the production of prodrugs. Due to the polyfunctionality of the intermediates, and the known catalytic decomposition of simple alkyl carbonochloridates, acylation reactions like the one used in providing the desired prodrugs could be expected to be troublesome, but this turned out not to be so, as illustrated by the non-optimized reactions of I with a few hydroxyl or amino group containing compounds (Examples 16–21). The present intermediates are effective means in the production of the prodrugs in question, and they provide said final prodrugs in good yields in one step processes.

The invention shall in the following be further illustrated. The numbers and number/letter combinations used refer to Scheme A, to the Tables 1–10 and to the Examples given in the following.

| (4–5) | $R^2$ |
|---|---|
| a | $CH_3$ |
| b | $CH_3CH_2$ |
| c | $CH_3(CH_2)_3$ |
| d | 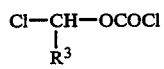 |
| e | 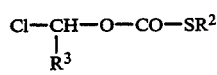 |

| (6) | $R^1$ | $R^2$ |
|---|---|---|
| ab | H | $CH_3CH_2$ |
| ba | $CH_3$ | $CH_3$ |
| bb | $CH_3$ | $CH_3CH_2$ |
| ca | $CH_3CH_2$ | $CH_3$ |
| cb | $CH_3CH_2$ | $CH_3CH_2$ |
| cc | $CH_3CH_2$ | $CH_3(CH_2)_3$ |
| da | $CH_3(CH_2)_2$ | $CH_3$ |
| db | $CH_3(CH_2)_2$ | $CH_3CH_2$ |
| dd | $CH_3(CH_2)_2$ |  |
| eb | $CH_3(CH_2)_3$ | $CH_3CH_2$ |
| fb | $(CH_3)_3C$ | $CH_3CH_2$ |
| fc | $(CH_3)_3C$ | $CH_3(CH_2)_3$ |
| fe | $(CH_3)_3C$ | 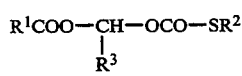 |
| gb | $CH_3(CH_2)_4$ | $CH_3CH_2$ |
| hb | $CH_3(CH_2)_5$ | $CH_3CH_2$ |
| ib | $CH_3(CH_2)_6$ | $CH_3CH_2$ |
| jb | $CH_3(CH_2)_7$ | $CH_3CH_2$ |
| kb | $CH_3(CH_2)_{12}$ | $CH_3CH_2$ |
| lb | 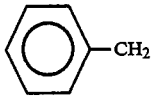 | $CH_3CH_2$ |
| mb |  | $CH_3CH_2$ |
| nb | $CH_3\overset{\displaystyle OH}{\underset{\displaystyle }{CH}}{}^{\diagup}$ | $CH_3CH_2$ |
| ob | $CH_3\overset{O}{\underset{\|}{C}}$ | $CH_3CH_2$ |
| pb | $CH_3\overset{O}{\underset{\|}{C}}(CH_2)_2$ | $CH_3CH_2$ |
| qb | $CH_3CH_2OCH_2$ | $CH_3CH_2$ |
| rb | 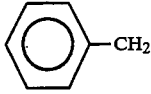 | $CH_3CH_2$ |
| sb | $F_3C$ | $CH_3CH_2$ |

-continued

| | | |
|---|---|---|
| tb | CH₃C(=O)NHCH₂ | CH₃CH₂ |
| ub | (pyrrolidinone with SO₂(CH₃)₂) | CH₃CH₂ |

| (7) | R¹ |
|---|---|
| b | CH₃ |
| c | CH₃CH₂ |
| d | CH₃(CH₂)₂ |
| e | CH₃(CH₂)₃ |
| f | (CH₃)₃C |
| g | CH₃(CH₂)₄ |
| h | CH₃(CH₂)₅ |
| i | CH₃(CH₂)₆ |
| j | CH₃(CH₂)₇ |
| k | CH₃(CH₂)₁₂ |
| l | (phenyl) |
| m | (furyl) |
| o | CH₃C(=O) |
| p | CH₃C(=O)(CH₂)₂ |
| q | CH₃CH₂OCH₂ |
| r | C₆H₅OCH₂ |

-continued

| (8) | R¹ | Nu |
|---|---|---|
| c1 | CH₃CH₂ | Cl-C₆H₄-NH |
| c2 | CH₃CH₂ | CH₃O |
| c3 | CH₃CH₂ | CH₃CH₂CH(CH₃)O |
| c4 | CH₃CH₂ | C₆H₅CH₂CH₂O |
| c5 | CH₃CH₂ | NO₂-C₆H₄-O |

TABLE 1

O-Chloromethyl S-Alkyl or S-Aryl Carbonothioates 4 Prepared

| Product | Method | Yield$^a$ (%) | b.p. (°C.) mbar | Purity$^b$ (%) | Molecular Formula$^c$ | IR (CHCl₃)$^d$ $\nu$-SCO— (cm⁻¹) |
|---|---|---|---|---|---|---|
| 4a | B | 41 | 62–66/17 | 90 | C₃H₅ClO₂S (140.6) | 1725 |
| 4b | A | 81 | 67–70/14 | 95 | C₄H₇ClO₂S (154.6) | 1720 |
| 4b | B | 49 | | 90 | | |
| 4c | B | 72 | 99–101/24 | 84 | C₆H₁₁ClO₂S (182.7) | 1720 |
| 4d | A | 99 | 90–92/0.2 | 95 | C₈H₇ClO₂S (202.7) | 1740 |
| 4d | B | 18 | | 90 | | |
| 4e | B | 90 | 103–105/0.6 | 90 | C₉H₉ClO₂S (216.7) | 1722 |

$^a$Yield (unoptimized) of isolated product.
$^b$Estimated by ¹H-NMR.
$^c$Satisfactory microanalyses obtained (C, H, S, Cl ± 0.4%).
$^d$Recorded on a Perkin-Elmer 783 infrared spectrophotometer (10% in CHCl₃).

TABLE 2

¹H-NMR of Products 4 (CDCl₃/TMS)

| Product | ClCH₂O (s, 2H) | R² |
|---|---|---|
| 4a$^a$ | 5.78 | 2.40 (s, 3H, CH₃) |
| 4b$^b$ | 5.72 | 1.31 (t, 3H, J=7 Hz, CH₃); 2.90 (q, 2H, J=7 Hz, CH₂) |
| 4c$^c$ | 5.76 | 0.93 (t, 3H, J=7 Hz, CH₃); 1.2–1.8 (m, 4H, CH₃CH₂CH₂); 2.92 (t, 2H, J=7 Hz, SCH₂) |
| 4d$^b$ | 5.70 | 7.50 (bs, 5H, Ph) |
| 4e$^c$ | 5.71 | 4.13 (s, 2H, CH₂); 7.29 (bs, 5H, Ph) |

$^a$Recorded at 300 MHz on a Brucker AC-300 spectrometer.
$^b$Recorded at 60 MHz on a Jeol PMX-60 spectrometer.
$^c$Recorded at 100 MHz on a Jeol FX-100 spectrometer.

TABLE 3

O-Iodomethyl S-Alkyl or S-Aryl Carbonothioates 5 Prepared

| Product | Yield$^a$ (%) | Isolated NaCl (%) | Purity$^b$ (%) | Molecular Formula$^c$ | IR (CHCl₃)$^d$ $\nu$-SCO— (cm⁻¹) |
|---|---|---|---|---|---|
| 5a | 96 | 96 | | C₃H₅IO₂S (232.0) | |

TABLE 3-continued

O-Iodomethyl S-Alkyl or S-Aryl Carbonothioates 5 Prepared

| Product | Yield[a] (%) | Isolated NaCl (%) | Purity[b] (%) | Molecular Formula[c] | IR (CHCl3)[d] $\nu$-SCO— (cm$^{-1}$) |
|---|---|---|---|---|---|
| 5b | 96 | 95 | 90 | $C_4H_7IO_2S$ (246.1) | 1720 |
| 5b[e] | 94 |  | 95–100 |  |  |
| 5c | 97 | 98 |  | $C_6H_{11}IO_2S$ (274.1) |  |
| 5d | 95 | 94 | 95 | $C_8H_7IO_2S$ (294.1) |  |
| 5e | 97 | 96 |  | $C_9H_9IO_2S$ (308.1) |  |

[a]Yield (unoptimized) of isolated product (not distilled).
[b]Estimated by $^1$H-NMR.
[c]No microanalyses obtained.
[d]Recorded on a Perkin Elmer 783 infrared spectrophotometer (10% in CHCl3)
[e]Optimized method.

TABLE 4

$^1$H-NMR of Products 5 (CDCl3/TMS)[a]

| Product | JCH2O (s, 2 H) | R$^2$ |
|---|---|---|
| 5b | 5.98 | 1.31(t, 3H, J=7–8Hz, CH3)<br>1.92(q, 2H, J=7–8Hz, CH2) |
| 5d | 5.95 | 7.10–7.90(m, 5H, Ph) |

[a]Recorded at 60 MHz on a Jeol PMX-60 spectrometer

TABLE 5

O-Acyloxymethyl S-Alkyl or S-Aryl Carbonothioates 6 Prepared

| Product | Method | Yield[a] (%) | b.p. (°C.) mbar | Purity[b] (%) | Molecular Formula | IR (CHCl3)[c] $\nu$-SCO— (cm$^{-1}$) | $\nu$-OCR$^1$ (cm$^{-1}$) |
|---|---|---|---|---|---|---|---|
| 6ab[d] | C | 53 | 52–54/0.4 | 80 | $C_5H_8O_4S$[e] (164.2) | 1735 | (Broad) |
| 6ba | C | 48 | 54–55/0.4 | 90 | $C_5H_8O_4S$[e] (164.2) | 1720 | 1760 |
| 6bb | C | 64 | 62–64/0.5 | 75 | $C_6H_{10}O_4S$[e] (178.2) | 1720 | 1765 |
| 6bb | F | 17 | 50/0.3 | 90 | [f] |  |  |
| 6ca | C | 43 | 58/0.4 | 85 | $C_6H_{10}O_4S$[f,g] (178.2) | 1720 | 1760 |
| 6cb | C | 70 | 72–74/0.3 | 90 | $C_7H_{12}O_4S$[f,h] (192.2) | 1720 | 1760 |
| 6cb | D[i,j] | 98 | 71–73/0.3 | 95–100 | [e] |  |  |
| 6cc | C | 50 | 87/0.5 | 70 | $C_9H_{16}O_4S$[k] (220.3) | 1720 | 1760 |
| 6da | C | 98 | 68–70/0.6 | 90 | $C_7H_{12}O_4S$[e] (192.2) | 1722 | 1760 |
| 6db | C | 76 | 75–80/0.5 | 95 | $C_8H_{14}O_4S$[e] (206.2) | 1720 | 1760 |
| 6db | D[i] | 92 |  | 95 |  |  |  |
| 6db | J | 87 |  | 80–85 |  |  |  |
| 6dd | C | 72 | 113–130/0.4[l] | 85 | $C_{12}H_{14}O_4S$[e] (254.3) | 1735 | 1760 (shoulder) |
| 6eb | C | 66 | 80–84/0.2 | 75 | $C_9H_{16}O_4S$[e] (220.3) | 1720 | 1760 |
| 6fb | C | 65 | 66–68/0.4 | 90 | $C_9H_{16}O_4S$[m] (220.3) | 1720 | 1750 |
| 6fc | C | 72 | 90–92/0.6 | 90 | $C_{11}H_{20}O_4S$[f,h] (248.3) | 1720 | 1750 |
| 6fe | C | 69 | 136–140/0.3 | 90 | $C_{14}H_{18}O_4S$[f,o] (282.4) | 1720 | 1750 |
| 6gb | C | 62 | 92–96/0.3 | 90 | $C_{10}H_{18}O_4S$[e] (234.3) | 1720 | 1755 |
| 6hb | D[p] | 85 | 98–104/0.3 | 85 | $C_{11}H_{20}O_4S$[e] (248.3) | 1720 | 1755 |
| 6ib | D[p] | 78 |  | 90 | $C_{12}H_{22}O_4S$[e] (262.4) | 1720 | 1755 |
| 6jb | D[p] | 87 |  | 80 | $C_{13}H_{24}O_4S$[e] (276.4) | 1720 | 1755 |
| 6kb | E | 99 |  | 80 | $C_{18}H_{34}O_4S$[k] (346.5) | 1720 | 1760 |
| 6kb | D[p] | 94 |  | 95 |  |  |  |
| 6lb | C | 64 | 122–24/0.2 | 90 | $C_{11}H_{12}O_4S$[f] (240.3) | 1725 (shoulder) | 1740 |
| 6mb | D[i] | 74 | 37.2–38.4[q] | 95 | $C_9H_{10}O_5S$[f] | 1720 | 1740 |

TABLE 5-continued

O-Acyloxymethyl S-Alkyl or S-Aryl Carbonothioates 6 Prepared

| Product | Method | Yield[a] (%) | b.p. (°C.) mbar | Purity[b] (%) | Molecular Formula | IR (CHCl$_3$)[c] $\nu$-SCO— (cm$^{-1}$) $\overset{O}{\underset{\parallel}{}}$ | IR (CHCl$_3$)[c] $\nu$-OCR$^1$ (cm$^{-1}$) $\overset{O}{\underset{\parallel}{}}$ |
|---|---|---|---|---|---|---|---|
| 6nb[d] | C | 54 | 110–14/0.3 | 90 | C$_7$H$_{12}$O$_5$S[f,r] (230.2) (208.2) | 1720 | 1760 |
| 6ob | C | 28 | 90–94/0.3 | 90 | C$_7$H$_{10}$O$_5$S[f] (206.2) | 1720 | 1755 (1740 α-keto) |
| 6ob | D[i] | 50 | | 90 | e | | |
| 6pb | D[i] | 75 | 130–140/0.4 | 90 | C$_9$H$_{14}$O$_5$S[f] (234.3) | 1720 (broad) | 1760 |
| 6qb | D[s] | 34 | 91/0.1 | 90 | C$_8$H$_{14}$O$_5$S[e] (222.3) | 1720 | 1780 |
| 6rb | D[i] | 95 | 49–50[q] | 99 | C$_{12}$H$_{14}$O$_5$S[f] (270.3) | 1720 | 1780 |
| 6sb[d] | F | 42 | 40/0.3 | 75 | C$_6$H$_7$F$_3$O$_4$S[e] (232.2) | 1725 | 1805 |
| 6tb[d] | F | 46 | | 90 | C$_8$H$_{13}$NO$_5$S[e] (235.3) | 1720 | 1760 (1680 amide) |
| 6ub[d] | D[i] | 62 | 81.5–83[q] | 95 | C$_{12}$H$_{17}$NO$_7$S$_2$[f] (351.4) | 1720 | 1780 (1800 β-lactam) |

[a]Yield (unoptimized) of isolated product.
[b]Estimated by $^1$H-NMR.
[c]Recorded on a Perkin Elmer 783 infrared spectrophotometer (10% in CHCl$_3$).
[d]Not transformed into the derived carbonochloridate 7.
[e]Not analysed.
[f]Satisfactory microanalyses obtained (C, H, S (N) ± 0.4%).
[g](C: +1.0%, S: −1.7%).
[h](S: −0.7%).
[i]Organic phase: methylene chloride.
[j]Optimized method.
[k]Unsatisfactory microanalyses obtained.
[l]Product decomposes during distillation.
[m]Purified by column chromatography on SiO$_2$(Merck 60, n-hexane/ethyl acetate, 9:1) to obtain satisfactory microanalyses.
[n](C: +0.65%; S: +1.00%).
[o](C: −0.6%; S: +0.45).
[p]Organic phase: ethyl acetate.
[q]Melting point, uncorrected, obtained on a Büchi 510 apparatus.
[r](C: +0.45%).
[s]Organic phase: ethylene chloride.

TABLE 6

$^1$H-NMR of Products 6 (CDCl$_3$/TMS).

| Product | R$^1$ | OCH$_2$O (s, 2H) | R$^2$ |
|---|---|---|---|
| 6ab[a] | 8.05 (s, 1H, H) | 5.85 | 1.32 (t, 3H, J=7.5 Hz, CH$_3$) 2.92 (q, 2H, J=7.5 Hz, CH$_2$) |
| 6ba[b] | 2.12 (s, 3H, CH$_3$) | 5.79 | 2.37 (s, 3H, CH$_3$) |
| 6bb[b] | 2.12 (s, 3H, CH$_3$) | 5.79 | 1.33 (t, 3H, J=7.5 Hz, CH$_3$) 2.90 (q, 2H, J=7.5 Hz, CH$_2$) |
| 6ca[b] | 1.16 (t, 3H, J=7.5 Hz, CH$_3$) 2.40 (q, 2H, J=7.5 Hz, CH$_2$) | 5.81 | 2.36 (s, 3H, CH$_3$) |
| 6cb[a] | 1.16 (t, 3H, J=7.5 Hz, CH$_3$) 2.40 (q, 2H, J=7.5 Hz, CH$_2$) | 5.81 | 1.33 (t, 3H, J=7.5 Hz, CH$_3$) 2.90 (q, 2H, J=7.5 Hz, CH$_2$) |
| 6cc[b] | 1.16 (t, 3H, J=7.5 Hz, CH$_3$) 2.40 (q, 2H, J=7.5 Hz, CH$_2$) | 5.80 | 0.93 (t, 3H, J=7 Hz, CH$_3$) 1.2–1.8 (m, 4H, CH$_3$CH$_2$CH$_2$) 2.89 (t, 2H, J=7 Hz, CH$_2$S) |
| 6da[b] | 0.96 (t, 3H, J=7 Hz, CH$_3$) 1.5–1.9 (m, 2H, CH$_3$CH$_2$CH$_2$) 2.3 (m, 2H, COCH$_2$) | 5.81 | 2.36 (s, 3H, CH$_3$) |
| 6db[a] | 0.96 (t, 3H, J=7 Hz, CH$_3$) 1.7 (m, 2H, CH$_3$CH$_2$CH$_2$) 2.35 (t, 2H, J=7 Hz, COCH$_2$) | 5.77 | 1.30 (t, 3H, J=7.5 Hz, CH$_3$) 2.88 (q, 2H, J=7.5 Hz, CH$_2$) |
| 6dd[a] | 0.95 (t, 3H, J=7 Hz, CH$_3$) 1.3–2.0 (m, 2H, CH$_3$CH$_2$CH$_2$) 2.35 (t, 2H, J=7 Hz, COCH$_2$) | 5.89 | 7.1–7.8 (m, 5H, Ph) |
| 6eb[a] | 0.8–2.0 (m, 7H, CH$_3$CH$_2$CH$_2$) 2.39 (t, 2H, J=7 Hz, COCH$_2$) | 5.79 | 1.31 3H, J=7.5 Hz, CH$_3$) 2.91 (q, 2H, J=7.5 Hz, CH$_2$) |
| 6fb[a] | 1.25 (s, 9H, (CH$_3$)$_3$C) | 5.80 | 1.31 (t, 3H, J=7.5 Hz, CH$_3$) 2.91 (q, 2H, J=7.5 Hz, CH$_2$) |
| 6fc[b] | 1.22 (s, 9H, (CH$_3$)$_3$C) | 5.80 | 0.92 (t, 3H, J=7 Hz, CH$_3$) 1.2–1.9 (m, 4H, CH$_3$CH$_2$CH$_2$) 2.88 (t, 2H, J=7 Hz, CH$_2$S) |
| 6fe[b] | 1.20 (s, 9H, (CH$_3$)$_3$C) | 5.79 | 4.11 (s, 2H, CH$_2$) 7.29 (bs, 5H, Ph) |
| 6gb[a] | 0.8–2.0 (m, 6H, CH$_3$CH$_2$CH$_2$CH$_2$) 0.9 (t, 3H, J=7 Hz, CH$_3$) 2.38 (t, 2H, J=7 Hz, COCH$_2$) | 5.79 | 1.32 (t, 3H, J=7.5 Hz, CH$_3$) 2.90 (q, 2H, J=7.5 Hz, CH$_2$) |
| 6hb[a] | 0.7–2.0 (m, 8H, CH$_3$(CH$_2$)$_4$) | 5.80 | 1.31 (t, 3H, J=7.5 Hz, CH$_3$) |

TABLE 6-continued

$^1$H-NMR of Products 6 (CDCl$_3$/TMS).

| Product | R$^1$ | OCH$_2$O (s, 2H) | R$^2$ |
|---|---|---|---|
| | 0.9 (t, 3H, J=7 Hz, CH$_3$) | | 2.90 (q, 2H, J=7.5 Hz, CH$_2$) |
| | 2.35 (t, 2H, J=7 Hz, COCH$_2$) | | |
| 6ib[a] | 0.7–2.0 (m, 10H, CH$_3$(CH$_2$)$_5$ | 5.80 | 1.30 (t, 3H, J=7.5 Hz, CH$_3$) |
| | 0.9 (t, 3H, J=7 Hz, CH$_3$) | | 2.90 (q, 2H, J=7.5 Hz, CH$_2$) |
| | 2.38 (t, 2H, J=7 Hz, COCH$_2$) | | |
| 6jb[b] | 0.88 (bt, 3H, CH$_3$ | 5.80 | 1.33 (t, 3H, J=7.5 Hz, CH$_3$) |
| | 1.27 (m, 10H, CH$_3$(CH$_2$)$_5$) | | 2.89 (q, 2H, J=7.5 Hz, CH$_2$) |
| | 1.60 (m, 2H, CH$_2$CH$_2$CO) | | |
| | 2.37 (t, 2H, COCH$_2$) | | |
| 6kb[b] | 0.88 (bt, 3H, CH$_3$) | 5.80 | 1.33 (t, 3H, J=7.5 Hz, CH$_3$) |
| | 1.26 (m, 20H, CH$_3$(CH$_2$)$_{10}$) | | 2.89 (q, 2H, J=7.5 Hz, CH$_2$) |
| | 1.60 (m, 2H, CH$_2$CH$_2$CO) | | |
| | 2.37 (t, 2H, COCH$_2$) | | |
| 6lb[a] | 7.2–7.8 (m, 2H, arom) | 6.01 | 1.30 (t, 3H, J=7.5 Hz, CH$_3$) |
| | 7.95–8.3 (m, 2H arom) | | 2.89 (q, 2H, J=7.5 Hz, CH$_2$) |
| 6mb[b] | 6.55 (m, 1H arom) | 6.01 | 1.33 (t, 3H, J=7.5 Hz, CH$_3$) |
| | 7.3 (m, 1H arom) | | 2.90 (q, 2H, J=7.5 Hz, CH$_2$) |
| | 7.65 (m, 1H arom) | | |
| 6nb[a] | 1.41 (d, 3H, CH$_3$) | 5.85 | 1.32 (t, 3H, J=7.5 Hz, CH$_3$) |
| | 3.0 (bs, 1H, OH) | | 2.90 (q, 2H, 7=7.5 Hz, CH$_2$) |
| | 4.35 (bq, 1H, CH) | | |
| 6ob[b] | 2.50 (s, 3H, CH$_3$) | 5.93 | 1.34 (t, 3H, J=7.5 Hz, CH$_3$) |
| | | | 2.91 (q, 2H, J=7.5 Hz, CH$_2$) |
| 6pb[a] | 2.16 (s, 3H, CH$_3$) | 5.79 | 1.31 (t, 3H, J=7.5 Hz, CH$_3$) |
| | 2.8 (m, 4H, (CH$_2$)$_2$) | | 2.90 (q, 2H, J=7.5 Hz, CH$_2$) |
| 6qb[a] | 1.22 (t, 3H, J=7 Hz, CH$_3$) | 5.85 | 1.32 (t, 3H, J=7.5 Hz, CH$_3$) |
| | 3.6 (q, 2H, J=7 Hz, CH$_2$O) | | 2.91 (q, 2H, J=7.5 Hz, CH$_2$) |
| | 4.12 (s, 2H, OCH$_2$CO) | | |
| 6rb[a] | 4.65 (s, 2H, OCH$_2$CO) | 5.85 | 1.32 (t, 3H, J=7.5 Hz, CH$_3$) |
| | 6.8–7.6 (m, 5H, Ph) | | 2.91 (q, 2H, J=7.5 Hz, CH$_2$) |
| 6sb[a] | | 5.95 | 1.33 (t, 3H, J=7.5 Hz, CH$_3$) |
| | | | 2.92 (q, 2H, J=7.5 Hz, CH$_2$) |
| 6tb[a] | 2.05 (s, 2H, CH$_3$) | 5.80 | 1.33 (t, 3H, J=7.5 Hz, CH$_3$) |
| | 4.08 (d, 2H, J=5 Hz, CH$_2$) | | 2.90 (q, 2H, J=7.5 Hz, CH$_2$) |
| | 6.0–6.6 (m, 1H, NH) | | |
| 6ub[b] | 1.42, .60 (2s, 3H each, 2CH$_3$) | 5.78, 5.97 | 1.34 (t, 3H, J=7.5 Hz, CH$_3$) |
| | 3.40 (m, 2H, CHCH$_2$CON), | (ABq, 2H, J=5.8 Hz) | 2.91 (q, 2H, J=7.5 Hz, CH$_2$) |
| | 4.42 (s, 1H, (CH$_3$)$_2$CCHCOO) | | |
| | 4.63 (dd, 1H, J=2.8 and 3.7) | | |
| | SO$_2$CHCH$_2$) | | |

[a]Recorded at 60 MHz on a Jeol PMX-60 spectrometer.
[b]Recorded at 100 MHz on a Jeol FX-100 spectrometer.

TABLE 7

Acyloxymethyl Carbonochloridates 7 Prepared

| Product | Method | Yield[a] (%) | Purity[b] (%) | From | b.p. (°C.) mbar | Molecular Formula | IR[c] $\nu$-ClCO— (cm$^{-1}$) | $\nu$-OCR$^1$ (cm$^{-1}$) |
|---|---|---|---|---|---|---|---|---|
| 7b | G | 50 | 90 | 6ba | 62/13 | C$_4$H$_5$ClO$_4$[d] (152.5) | 1785 (broad) | |
| 7b | G | 63 | 80 | 6bb | 60–62/13 | [d] | | |
| 7c | G | 31 | 85 | 6cb | 72.5/16 | C$_5$H$_7$ClO$_4$[e,f] (166.0) | 1780 (broad) | |
| 7c | H | 86 | 95 | 6cb | 70–71/13 | [e,g] | | |
| 7d | G | 60 | 95 | 6da | 82–84/13 | C$_6$H$_9$ClO$_4$[d] (180.6) | 1780 (broad) | |
| 7d | G | 91 | 90 | 6db | 80–82/13 | [d] | | |
| 7d | G | | | 6dd | [h] | | | |
| 7e | G | 88 | 85 | 6eb | 90–94/13 | C$_7$H$_{11}$ClO$_4$[d] (194.6) | 1780 (broad) | |
| 7f | G | 60 | 95 | 6fb | 73–75/13 | C$_7$H$_{11}$ClO$_4$[d] (194.6) | 1785 | 1760 |
| 7f | G[i] | | | 6fc | [j] | | | |
| 7f | G[i] | | | 6fe | [j] | | | |
| 7g | G | 77 | 90 | 6gb | 65–67/0.2 | C$_8$H$_{13}$ClO$_4$[d] (208.6) | 1780 (broad) | |
| 7h | G | 56 | 85 | bhb | 75–78/0.3 | C$_7$H$_{15}$ClO$_4$[d] (198.7) | 1780 (broad) | |
| 7i | G | 61 | 95 | 6ib | 80–90/0.3 | C$_{10}$H$_{17}$ClO$_4$[d] (236.7) | 1780 (broad) | |
| 7j | G | 100 | 85 | 6jb | | C$_{11}$H$_{19}$ClO$_4$[d] (250.7) | 1780 (broad) | |
| 7k | G | 100 | 85 | 6kb | | C$_{16}$H$_{29}$ClO$_4$[d] (320.9) | 1780 (broad) | |

TABLE 7-continued

Acyloxymethyl Carbonochloridates 7 Prepared

| Product | Method | Yield[a] (%) | Purity[b] (%) | From | b.p. (°C.) mbar | Molecular Formula | IR[c] $\nu$-ClCO— (cm$^{-1}$) | IR[c] $\nu$-OCR$^1$ (cm$^{-1}$) |
|---|---|---|---|---|---|---|---|---|
| 7l | G | 65 | 95 | 6lb | 102–103/0.3 | C$_9$H$_7$ClO$_4$[e,k] (214.6) | 1780 | 1745 |
| 7m | G[i] | 96 | 85 | 6mb | | C$_7$H$_7$ClO$_5$[d] (204.6) | 1780 | 1750 |
| 7o | G | 70 | 85 | 6ob | 80–90/0.3 | C$_5$H$_5$ClO$_5$[d] (180.5) | 1780 | 1760 (1740 α-keto) |
| 7p | G | 28 | 75 | 6pb | 110–20/1.3 | C$_7$H$_9$ClO$_5$[d] (208.6) | 1765 (broad) | (1720 γ-keto) |
| 7q | G | 48 | 80 | 6qb | 78/0.3 | C$_6$H$_9$ClO$_5$[d] (196.6) | 1790 | |
| 7r | G[i,l] | 98 | 80 | 6rb | | C$_{10}$H$_9$ClO$_5$[d] (244.6) | 1790 (broad) | |

[a]Yield (unoptimized) of isolated product.
[b]Estimated by $^1$H-NMR.
[c]Recorded on a Perkin-Elmer 783 spectrophotometer (10% in CHCl$_3$).
[d]Not analysed.
[e]Satisfactory microanalyses obtained (C, H, Cl ± 0.4%).
[f](S: +1.5%).
[g](S: +0.7%).
[h]Not purifiable by distillation.
[i]Reaction in 10% CH$_2$Cl$_2$ solution.
[j]Not obtainable in a satisfactory purity.
[k](S: +0.95%).
[l]Reaction in 10% CH$_3$CN solution.

TABLE 8

$^1$H-NMR of Products 7 (CDCl$_3$/TMS)

| Product | R$^1$ | OCH$_2$O (s, 2H) |
|---|---|---|
| 7b[a] | 2.13 (s, 3H, CH$_3$) | 5.78 |
| 7c[b] | 1.18 (t, 3H, J=7.5 Hz, CH$_3$)<br>2.38 (q, 2H, J=7.5 Hz, CH$_2$) | 5.83 |
| 7d[b] | 0.98 (t, 3H, J=7 Hz, CH$_3$)<br>1.73 (m, 2H, CH$_3$CH$_2$)<br>2.47 (t, 2H, J=7 Hz, COCH$_2$) | 5.82 |
| 7e[b] | 0.93 (t, 3H, J=7 Hz, CH$_3$)<br>1.2–1.9 (m, 4H, CH$_3$(CH$_2$)$_2$)<br>2.42 (t, 2H, J=7 Hz, COCH$_2$) | 5.82 |
| 7f[a] | 1.22 (s, 9H, (CH$_2$)$_3$C) | 5.81 |
| 7g[a] | 0.90 (t, 3H, J=7 Hz, CH$_3$)<br>1.0–2.0 (m, 6H, CH$_3$(CH$_2$)$_3$)<br>2.40 (t, 2H, J=7 Hz, COCH$_2$) | 5.80 |
| 7h[a] | 0.90 (t, 3H, J=7 Hz, CH$_3$)<br>1.0–2.0 (m, 8H, CH$_3$(CH$_2$)$_4$)<br>2.45 (t, 2H, J=7 Hz, COCH$_2$) | 5.83 |
| 7i[a] | 0.90 (t, 3H, J=7 Hz, CH$_3$)<br>1.0–2.0 (m, 10H, CH$_3$(CH$_2$)$_5$)<br>2.44 (t, 2H, J=7 Hz, COCH$_2$) | 5.83 |
| 7j[a] | 0.90 (t, 3H, J=7 Hz, CH$_3$)<br>1.0–2.0 (m, 12H, CH$_3$(CH$_2$)$_6$)<br>2.44 (t, 2H, J=7 Hz, COCH$_2$) | 5.83 |
| 7k[a] | 0.90 (t, 3H, J=7 Hz, CH$_3$)<br>0.8–2.0 (m, 22H, CH$_3$(CH$_2$)$_{11}$)<br>2.44 (t, 2H, J=7 Hz, COCH$_2$) | 5.81 |
| 7l[a] | 7.2–77 (m, 3H arom)<br>8.0–8.3 (m, 2H arom) | 6.03 |
| 7m[a] | 6.6 (dd, 1H arom, J=4 and 2 Hz)<br>7.32 (d, 1H arom, J=4 Hz)<br>7.65 (bs, 1H arom) | 6.02 |
| 7o[b] | 2.52 (s, 3H, CH$_3$) | 5.96 |
| 7p[a] | 2.19 (s, 3H, CH$_3$)<br>2.75 (m,, 4H, CH$_2$CH$_2$) | 5.70 |
| 7q[a] | 1.22 (t, 3H, J=7 Hz, CH$_3$)<br>3.60 (q, 2H, J=7 Hz, CH$_3$CH$_2$)<br>4.15 (s, 2H, OCH$_2$CO) | 5.83 |
| 7r[a] | 4.7 (s, 2H, OCH$_2$)<br>6.7–7.6 (m, 5H, Ph) | 5.85 |

[a]Recorded at 60 MHz on a Jeol PMX-60 spectrometer
[b]Recorded at 100 MHz on a Jeol PMX-100 spectrometer

TABLE 9

Acylation Products 8 Prepared.

| Product | Yield[a] (%) | b.p. (°C.) mbar | Purity[b] (%) | Molecular Formula | IR(CHCl$_3$)[c] $\nu$-SCO (cm$^{-1}$) |
|---|---|---|---|---|---|
| 8c1[d] | 31 | 90–91[e] | 95 | C$_{11}$H$_{12}$ClNO$_4$[f] (257.7) | 1755 (broad) |
| 8c1[g] | 71 | | 95–100 | | |
| 8c2[h] | 62 | 55–56/0.3 | 90 | C$_6$H$_{10}$O$_5$[i] (162.1) | 1760 (broad) |
| 8c3[h] | 49 | 66–68/0.5 | 95 | C$_9$H$_{16}$O$_5$[f] (204.2) | 1760 (broad) |
| 8c3[j] | 98[k] | | 95–100 | | |
| 8c4[h] | 36 | 120–22/0.3 | 85 | C$_{13}$H$_{16}$O$_5$[i] (252.31) | 1760 (broad) |
| 8c5[h] | 61 | 35–36[e] | 95–100 | C$_{11}$H$_{11}$NO$_7$[f] | 1775 (broad) |

TABLE 9-continued

Acylation Products 8 Prepared.

| Product | Yield[a] (%) | b.p. (°C.) mbar | Purity[b] (%) | Molecular Formula | IR(CHCl₃)[c] ν-SCO (cm⁻¹) |
|---|---|---|---|---|---|
| | | | | (269.21) | |

[a] Yield of isolated product.
[b] Estimated by NMR.
[c] Recorded on a Perkin Elmer 753 spectrophotometer (10% in CHCl₃).

[d] Using 2 eqv. 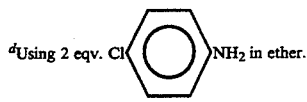 in ether.

[e] Melting point, uncorrected, obtained on a Büchi 510 apparatur.
[f] Satisfactory microanalyses obtained (C, H, (Cl, N) ± 0.4%).

[g] Using  in ether.

[h] Using  as a HCl scavenger.

[i] Not analysed.
[j] Using molecular sieve as a HCl scavenger.
[k] Not distilled.

TABLE 10

¹H-NMR of Products 8 (CDCl₃/TMS).

| | R¹ | | | |
|---|---|---|---|---|
| Product | CH₃ (t, 3H) J = 7.5 Hz | CH₂CO (q, 2H) | OCH₂O (s, 2H) | Nu |
| 8c1[a] | 1.15 | 2.39 | 5.81 | 7.05 (bs, 1H, NH) 7.25 (m, 4H arom) |
| 8c2[a] | 1.16 | 2.40 | 5.76 | 3.83 (s, 3H, CH₃) |
| 8c3[a] | 1.16 | 2.40 | 5.76 | 0.93 (t, 3H, J=7 Hz, CH₃CH₂) 1.29 (d, 3H, J=6 Hz, CH₃CH) 1.6 (m, 2H, CH₂) 4.74 (m, 1H, CH) |
| 8c4[a] | 1.14 | 2.38 | 5.73 | 2.98 (t, 2H, J=7 Hz, PhCH₂) 4.37 (t, 2H, J=7 Hz, CH₂CH₂O) 7.25 (bs, 5H, Ph) |
| 8c5[b] | 1.20 | 2.47 | 5.89 | 7.42 (m, 2H arom) 8.30 (m, 2H arom) |

[a] Recorded at 100 MHz on a Jeol FX-10 spectrometer.
[b] Recorded at 300 MHz on a Brucker AC-300 spectrometer.

EXAMPLE 1 (METHOD A)

O-Chloromethyl S-Ethyl Carbonothioate (4b)

A solution of ethanethiol (37 mL, 500 mmol) and Et₃N (Fluka, purum, 69.3 mL, 500 mmol) in Et₂O (200 mL) is added during 2 h to a stirred solution of 3 (44.0 mL, 500 mmol) in Et₂O (900 mL) at 0°–5° C. After stirring an additional 30 min. at 0°–5° C. and during the night at room temperature the resulting suspension is filtered. The filtrate is evaporated and the residue distilled to give 4b; yield: 57.9–62.6 g (75–81%), bp 67°–70° C./14 mbar.

EXAMPLE 2 (Method B)

O-Chloromethyl S-n-Butyl Carbonothioate (4c)

To a stirred 1M solution of NaOMe in MeOH (100 mL) at 0°–5° C. is dropwise added n-butanethiol (10.7 mL, 100 mmol). After evaporation to dryness the residue is suspended in Et₂O (200 mL) at −75° C. A solution of 3 (8.8 mL, 100 mmol) in Et₂O (50 mL) is added dropwise during 1 h with stirring followed by stirring overnight at ambient temperature. Evaporation of the solvent after filtration furnishes crude product which distilled yields 13.2 g (72%) of 4c, bp 99°–101° C./24 mbar.

EXAMPLE 3

O-Iodomethyl S-Ethyl Carbonothioate (5b)

The ester 4 b (15.4 g, 100 mmol) is added to a solution of NaI (22.5 g, 150 mmol) in Me₂CO (125 ml) and stirred for 3 h at 40° C. followed by filtration and washing with Me₂CO and Et₂O. The filtrate is evaporated and the residue partitioned (all solutions being ice-cold) between pentane (300 mL) and H₂O (100 mL). The organic phase is washed with aqueous 5% NaHCO₃ (50 mL), 1% aqueous Na₂S₂O₃ (50 mL, or more until colourlessness is achieved), H₂O (2×50 mL), dried (MgSO₄), and evaporated. Yield of crude product: 23.6 g (96%).

EXAMPLE 4 (Optimal procedure

The Procedure of Example 3 is slightly modified by increasing the amount of NaI to 30 g (200 ml), adding NaHCO₃ (0.8 g, 10 mmol), and heating at 40° C. for 4 h. Yield: 23.1 g (94%).

EXAMPLE 5 (Method C)

O-Butanoyloxymethyl S-Ethyl Carbonothioate (6db)

Crude 5b (23.6 g, 96 mmol) is added during 30 min to a stirred suspension of sodium butanoate (10.5 g, 96 mmol) in dry DMF (125 mL) at −20° C. followed by stirring overnight at ambient temperature. After filtration and washing with DMF (5 mL) and Et₂O (10 mL),Et₂O (250 mL) and ice-cold H₂O (100 mL) are added to the combined filtrates. The aqueous phase is separated and extracted with Et₂O (100 mL). The combined organic phases are washed (all solutions ice-cold) with 5% aqueous NaHCO₃ (50 mL), H₂O (50 mL), 0.01N HCl (100 mL), and H₂O (2×50 mL). After drying (MgSO₄) and evaporation of solvents the residue is

EXAMPLE 6 (Method D)

O-(2-Furancarbonyloxymethyl) S-Ethyl Carbonothioate (6mb)

2-Furancarboxylic acid (5.6 g, 50 mmol) is added to a stirred solution of NaHCO$_3$ (8.4 g, 100 mmol) and TBA HSO$_4$ (17.0 g, 50 mmol) in H$_2$O (100 mL) at room temperature. After stirring for 10 min 1,2-dichloroethane (100 mL) is added and the stirring continued for 30 min. 5b (12.5 g, 50 mmol) in 1,2-dichloroethane (25 mL) is added over 15 min. The mixture is stirred for 60 min at room temperature. The organic phase is separated, washed with H$_2$O (50 mL), dried (MgSO$_4$), and evaporated. The residue is stirred with Et$_2$O (100 mL), insoluble material filtered off and washed with Et$_2$O. The combined Et$_2$O-phases are evaporated and the residue crystallized from ice-cold pentane to yield 8.5 g (74%) of 6mb, mp 37.2°–38.4° C.

EXAMPLE 7 (Method D

O-Propanoyloxymethyl S-Ethyl Carbonothioate (6cb)

To a stirred solution of NaHCO$_3$ (45 g, 536 mmol) in H$_2$O (540 ml) is added TBA HSO$_4$ (91.2 g, 268 mmol), propanoic acid (20.1 mL, 268 mmol), and CH$_2$Cl$_2$ (540 ml). Following stirring for 1 h at room temperature a solution of 5b (49.2 g, 200 mmol) in CH$_2$Cl$_2$ (100 mL) is added during 45 min keeping the temperature below 30° C. The stirring is continued for 1½ h. The organic phase is separated, washed with H$_2$O (200 mL), dried (MgSO$_4$), and evaporated. The residue is stirred in Et$_2$O (800 mL) during the night, filtered, and washed with Et$_2$O (50 mL). The filtrate is evaporated and distilled to yield 38.0 g (98%) of 6cb, bp 71°–73° C./0.3 mbar.

EXAMPLE 8 (Method D)

O-(2-Oxopropanoyloxymethyl) S-Ethyl Carbonothioate (6ob)

Redistilled 2-oxopropanoic acid (12.6 ml, 0.18 mol) is added to a vigorously stirred mixture of NaHCO$_3$ (30.6 g, 0.36 mol), TBA HSO$_4$ (61.2 g, 0.18 mol), H$_2$O (360 mL), and CH$_2$Cl$_2$ (360 mL) in an open Erlenmeyer flask. Following stirring for 10 min 5b (44.0 g, 0.18 mol) in CH$_2$Cl$_2$ (400 mL) is added during 3 h at 25° C. together with CH$_2$Cl$_2$ (500 mL) in portions to compensate for the evaporation. In this way the formation of sulfurous by-products is minimized. The mixture is extracted with CH$_2$Cl$_2$ (300–200 mL). The combined organic phases are washed with H$_2$O (2×200 mL); dried (MgSO$_4$) and evaporated. The residue is triturated with Et$_2$O (600 mL). After filtration the filtrate is treated with charcoal, evaporated, and the residue crystallized from pentane at −70° C. to yield 6ob, melting below room temperature.

EXAMPLE 9 (Method D)

O-Tetradecanoyoxymethyl S-Ethyl Carbonothioate (6kb)

A THF solution (20 mL) of TBA tetradecanoate (8.4 g, 18 mmol), prepared by freeze-drying an aqueous solution of equimolar TBA OH and tetradecanoic acid, is slowly (30 min) added to a stirred solution of 5b (4.5 g, 18 mmol) in THF (20 mL) at room temperature. Following stirring during the night the precipitate formed is removed by filtration and washed with THF (5 mL). The filtrate is evaporated and the residue triturated with Et$_2$O (100 mL) and filtered. The filtrate leaves 6.2 g (99%) impure (80% by $^1$H-NMR) oily product after evaporation.

EXAMPLE 10 (Method F)

O-(N-Acetylglycyl)oxymethyl S-Ethyl Carbonothioate (6tb)

Finely powdered potassium N-acetylglycinate (5.8 g, 37 mmol) and TBA I (1.2 g, 3.4 mmol) are thoroughly mixed and shaken for 5 min with 5b (8.3 g, 34 mmol). The mixture is left for 48 h at room temperature and then extracted with Et$_2$O (4×40 mL). The combined extracts are filtered and evaporated. The residue (6.4 g) is thoroughly extracted with pentane (4×25 mL) to remove unreacted 5b. The residue is freed from remaining traces of pentane by evaporation leaving 3.7 g of 6tb (46%).

EXAMPLE 11 (Method G)

Butanoyloxymethyl Carbonochloridate (7d)

Redistilled SO$_2$Cl$_2$ (5.85 mL, 72 mmol) is added to 6db (14.8 g, 72 mmol) at 0°–5° C. with stirring during 15 min followed by stirring at room temperature (45 min). Evaporation at room temperature and 20 mbar during the night and distillation yields 11.8 g (91%) of 7d, bp 80°–82° C./13 mbar.

EXAMPLE 12 (Method H)

Propanoyloxymethyl Carbonochloridate (7c)

Redistilled SO$_2$Cl$_2$ (5.7 mL, 70 mmol) is added at once to 6cb (13.5 g, 70 mmol) at −25°–30° C. with stirring. After stirring at this temperature for 10 min BF$_3$.OEt$_2$ (0.3 mL) is added followed by stirring at 0° C. (1 h) and at room temperature (30 min). Evaporation at room temperature and 20 mbar (about 1 h) and subsequent distillation yields 10.0 g (86%) of 7c, bp 70°–71° C./13 mbar.

EXAMPLE 13

O-1-Chloroethyl S-Ethyl Carbonothioate

By following the procedure of Method A but replacing 3 by 1-chloroethyl carbonochloridate a 75% yield of the title compound is obtained with bp 71°–73° C./13 mbar. C$_5$H$_9$ClO$_2$S calc. C 35.61 H 5.40 Cl 21.02 S 19.01 (168.6) found 36.11 5.50 21.20 18.22 IR (10% CHCl$_3$): $\nu$=1715 cm$^{-1}$. NMR (CDCl$_3$/TMS)[44]: δ=1.31 (t, 3H, J=7 Hz, CH$_3$CH$_2$); 1.78 (d, 3H, J=6 Hz, CH$_3$CH); 2.90 (q, 2H, J=7 Hz, CH$_2$); 6.57 (q, 1H, J=6 Hz, CH).

EXAMPLE 14 (Method J)

O-1-Butanoyloxyethyl S-Ethyl Carbonothioate

To a stirred solution of TBA butanoate (32.9 g, 100 mmol), prepared by freeze-drying an aqueous solution of equimolar TBA OH and butanoic acid, in THF (500 ml) is added O1-chloroethyl S-ethyl carbonate (16.9 g, 100 mmol) at room temperature. Following stirring for 4 d and evaporation the residue is partioned between ice-cold Et$_2$O (600 mL) and H$_2$O (100 mL). The organic phase is extracted with H$_2$o (2×75 mL), dried (MgSO$_4$) and evaporated. The residue is distilled to yield 14.3 g (68%) of the title compound, bp 69°–72° C./0.3 mbar. C$_9$H$_{16}$O$_4$S calc. C 49.07 H 7.32 S 14.55 (220.3) found 48.73 7.38 14.94 IR (10% CHCl$_3$): $\nu$=1750 cm$^{-1}$. NMR (CDCl$_3$/TMS)[44]: δ=0.98 (t, 3H, J=7 Hz, CH$_3$(CH$_2$)$_2$); 1.31 (t, 3H, J=7.5 Hz, CH$_3$CH$_2$S); 1.48 (d, 3H, J=5 Hz, CH$_3$CH); 1.5–2.0 (m, 2H, CH$_3$CH$_2$CH$_2$); 2.31 (t, 2H, $\overline{J=7}$ Hz, CH$_2$CO); 2.88 (q, 2H, $\overline{J=7.5}$ Hz, CH$_2$S); 6.92 (q, 1H, J=5 Hz, CH).

EXAMPLE 15

1-Butanoyloxyethyl Carbonochloridate

Redistilled SO$_2$Cl$_2$ (0.2 mL, 2.5 mmol) is added to O-1-butanoyloxyethyl S-ethylcarbonothioate (0.55 g, 2.5 mmol) at −40° C. The temperature is slowly (0.5 h) raised to 0° C. followed by the addition of CCl$_4$ (5 mL) and BF$_3$.OEt$_2$ (3 drops). After stirring at 0° C. for 1 h CCl$_4$ (5 mL) is added and the solution half-way evaporated. Addition of CCl$_4$ (5 mL) and half-way evaporation is repeated three times to leave the title compound (80% purity by $^1$H-NMR) only stable in solution. IR (10% CCl$_4$): $\nu$=1760 cm$^{-1}$. $^1$H-NMR (CDCl$_3$:CCl$_4$ (1:1)/TMS)$^{45}$: $\delta$=0.98 (t, 3H, J=7.5 Hz, CH$_3$(CH$_2$)$_2$); 1.57 (d, 3H, J=5.5 Hz, CH$_3$CH); 1.6 (m, 2H, CH$_3$CH$_2$CH$_2$); 2.34 (t, 2H J=$\overline{7.5}$ Hz, CH$_2$CO); 6.80 (q, 1H, $\overline{J=5.5}$ Hz, CH).

EXAMPLE 16

Sec-Butyl Propanoyloxymethyl Carbonate (8c3)

To a solution of 2-butanol (0.92 mL, 10 mmol) and 4-methylmorpholine (1.1 mL, 10 mmol) in CHCl$_3$ (20 mL) at −70° C. is added 7c (1.7 g, 10 mmol) during 20 min with stirring. The temperature is kept at −70° C. for 1 h and then raised (1 h) to room temperature. Next day following evaporation the residue is triturated with Et$_2$O (25 mL) and filtered. The filtrate is evaporated and distilled to give 1.0 g (50%) of the title compound with bp 66°–68° C./5 mbar.

EXAMPLE 17

4-Nitrophenyl Propionyloxymethyl Carbonate (8c5)

4-Methylmorpholine (0.67 mL, 6.0 mmol) is added to a suspension of 4-nitrophenol (0.83 g, 6.0 mmol) in CH$_2$Cl$_2$ (10 mL) with stirring. A solution of 7c (1.27 g, 95% purity, 7.2 mmol) in CH$_2$Cl$_2$ (3 mL) is added during 20 min followed by stirring at 0° C. (30 min) and overnight at room temperature. After filtration the filtrate is evaporated and the residue partitioned between ice-cold Et$_2$O (25 mL) and H$_2$O (25 mL). The organic phase is extracted with ice-cold 0.5N NaOH (10 mL), H$_2$O (3×15 mL), dried (MgSO$_4$) and evaporated. The residue (1.50 g) is extracted with hexane (2×10 mL) to leave the title compound (0.98 g, 61%), mp 35°–36° C.

EXAMPLE 18

Propanoyloxymethyl 4-Chlorophenylcarbamate (8c1)

Me$_3$SiCl (2.3 mL, 18 mmol) is added to 4-chloroaniline (4.6 g, 36 mmol) in Et$_2$O (50 mL) at room temperature with stirring during 20 min. Following an additional 30 min stirring 7c (4.05 g, purity 90%, 22 mmol) in Et$_2$O (30 mL) is slowly (1 h) added. The stirring is continued overnight. The precipitate is filtered off and the filtrate extracted with ice-cold 0.1N HCl (50 mL), H$_2$O (3×50 mL), dried (MgSO$_4$) and evaporated. The residue (4.9 g) is extracted with hexane (50 mL) to leave 3.3 g (71%) of the title compound, mp 90°–91° C.

EXAMPLE 19

1-Butanoyloxyethyl 4-Chlorophenylcarbamate

A solution of 1-butanoyloxyethyl carbonochloridate (5 mmol) in CHCl$_3$ (10 mL) prepared as above but substituting CHCl$_3$ for CCl$_4$ is added to a solution of 4-chloroaniline (1.3 g, 10 mmol) in Et$_2$O (40 mL) at −70° C. Following stirring for 2 h at −70° C. and 3 h at −40° C. the mixture is kept at −20° C. for 3d. After filtration, treatment of the filtrate with charcoal, and evaporation of the filtrate the residue is triturated with ice-cold pentane (15 mL) and recrystallized from pentane (70 mL) to yield 0.4 g (28%) of the title compound with mp 52°–54° C. C$_{13}$H$_{16}$ClNO$_4$ calc. C 54.65 H 5.64 Cl 12.41 N 4.90 (285.7) found 54.72 5.64 12.31 4.83 IR (10% CHCl$_3$): $\nu$=1750 cm$^{-1}$. $^1$H-NMR (CDCl$_3$/TMS)$^{45}$: $\delta$=0.95 (t, 3H, J=7 Hz, CH$_3$(CH$_2$)$_2$CO); 1.50 (d, 3H, J=5.5 Hz, CH$_3$CH); 1.7 (m, 2H, CH$_3$CH$_2$CH$_2$CO); 2.31 (t, 2H, J=$\overline{7}$ Hz, CH$_2$CO); 6.8 (bs, 1H, $\overline{NH}$); 6.91 (q, 1H, J=5.5 Hz, CHCH$_3$); 7.28 (m, 4H arom.)

EXAMPLE 20

Sec-Butyl Propanoyloxymethyl Carbonate (8c3)

A mixture of 2-butanol (0.092 mL, 1 mmol), 7c (0.17 g, 1 mmol), and powdered molecular sieve (0.15 g, 4Å) in alcohol-free CHCl$_3$ (2 mL) is refluxed for 18 h. Following filtration through filter-aid and evaporation 0.2 g (98%) of the title compound is obtained.

EXAMPLE 21

D, L-N-Butanoyloxymethyleneoxycarbonyl-3,4-dihydroxyphenylalanine, dicyclohexylammonium salt

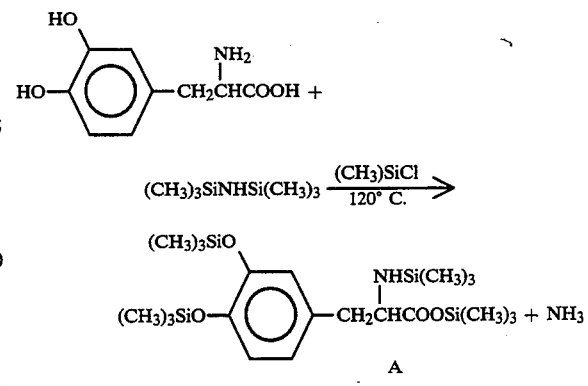

A mixture of 3-(3,4-dihydroxyphenyl)-D,L-alanine (2.0 g; 10 mmol), hexamethyldisilazane (7.36 ml; 40 mmol) and trimethylchlorosilane (4 drops), was heated at 120° C. for 3 hours under nitrogen. Excess of hexamethyldisilazane was distilled off in vacuo at 70° C./10 mmHg, in the end with xylene as a cosolvent to give A.

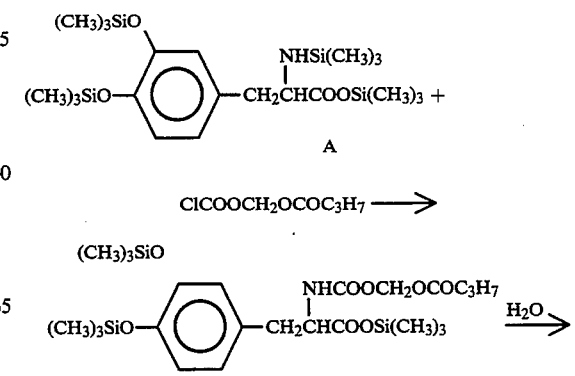

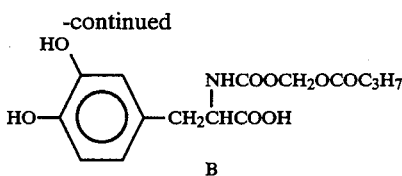

B

To A (10 mmol) in chloroform (15 ml) at −70° C. was added butanoyloxymethyl carbonochloridate (1.8 g, 10 mmol) in chloroform (5 ml). The temperature was slowly (over 2 hours) raised to 20° C., and the mixture stirred at 20° C. for hours. Then 5% extra butanoyloxymethyl carbonochloridate (~100 mg) was added, the mixture stirred at 20° C. for 3.5 hours and evaporated in vacuo. The residue was dissolved in tertiary butanol (100 ml), hydrolysed with water (10 ml) for 20 minutes, dried with MgSO₄ and evaporated in vacuo.

The residue was extracted twice with ether (100+50 ml) for 72 hours. The extracts were evaporated in vacuo to give 3.3 g of B.

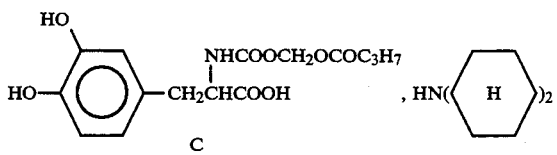

C

To a filtered solution of B (3.0 g; 8.8 mmol) in isopropyl ether (50 ml) at 0° C. was added dicyclohexylamine (1.75 ml; 8.8 mmol). The mixture was stirred at 0° C. for 15 minutes, the precipitate collected, washed with isopropyl ether (3×10 ml) and recrystallized first from acetone-ether (15/25 ml), then from acetone (40 ml) (60° C./0° C.) to yield 1.2 g (23%) of the title compound C with Mp: 135° C.

What we claim is:

1. An intermediate for the preparation of prodrugs, the intermediate having the formula I

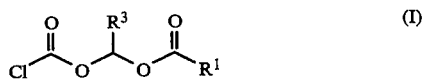

where $R^1$ stands for hydrogen or a straight or branched aliphatic $C_1$–$C_{20}$ carbon chain or an aryl or aralkyl group or a heterocyclic or heterocyclic alkyl group wherein the heterocyclic group is selected from the group consisting of furyl, thienyl, pyrdrolyl, imidazolyl, thiazolyl, oxazolyl, pyridyl and pyrimidinyl and $R^3$ is hydrogen or $C_1$–$C_3$ alkyl; $R^1$ unsubstituted or being substituted by hydroxy or halogen, and its chain being is uninterrupted or interrupted by oxygen, or by carbonyl group(s); and $R^3$ stands for hydrogen or $C_1$–$C_3$ alkyl.

2. An intermediate of formula I according to claim 1, in which $R^3$ stands for hydrogen.

3. An intermediate of formula I according to claim 1, in which $R^1$ stands for an aromatic or heterocyclic substituent selected from the group consisting of phenyl, furyl, thienyl, pyrrolyl, imidazolyl, thiazolyl, oxazolyl, pyridyl, and pyrimidinyl.

4. An intermediate according to claim 1, selected from the group consisting of
  a) acetyloxymethyl carbonochloridate,
  b) propanoyloxymethyl carbonochloridate,
  c) butanoyloxymethyl carbonochloridate,
  d) pentanoyloxymethyl carbonochloridate,
  e) benzoyloxymethyl carbonochloridate.

5. Method for producing an intermediate having formula I as follows:

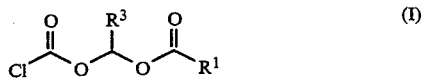

where $R^1$ stands for hydrogen or a straight or branched aliphatic $C_1$–$C_{20}$ carbon chain or an aryl or aralkyl group or a heterocyclic or heterocyclic alkyl group wherein the heterocyclic group is selected from the group consisting of furyl, thienyl, pyrdrolyl, imidazolyl, thiazolyl, oxazolyl pyridyl or pyrimidnyl, comprising, reacting a 1-haloalkyl carbonochloridate derivative of the formula IV $$Cl-\underset{\underset{R^3}{|}}{CH}-OCOCl \qquad (IV)$$

where $R^3$ is hydrogen or $C_1$–$C_3$ alkyl, with $R^2SR^4$, where $R^2$ is $C_1$–$C_4$ alkyl, and $R^4$ is hydrogen or an alkali metal ion, to form a 1-haloalkyl carbonothioate of the formula V

$R^2$ and $R^3$ having the above meanings, transforming the formed 1-haloalkyl carbonothioate into a 1-acyloxyalkyl carbonothioate of the formula VI

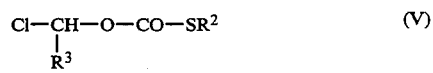

$R^1$, $R^2$ and $R^3$ having the above meanings, through a reaction with a salt of a carboxylic acid $R^1COOH$, $R^1$ having the above meanings, and finally reacting the 1-acyloxyalkyl carbothioate of formula VI with a chlorinating agent to yield the desired intermediate of formula I.

6. A method according to claim 5, wherein a compound according to formula I wherein $R^3$ is hydrogen, is prepared which comprises converting the compound of formula V to the corresponding iodide by reaction with sodium iodide, before transforming it via VI to I.

7. A method according to claim 5 or 6, in which the chlorinating agent is sulfuryl chloride.

* * * * *